United States Patent
Garigapati et al.

(10) Patent No.: US 9,265,857 B2
(45) Date of Patent: *Feb. 23, 2016

(54) ORGANOPHOSPHOROUS, MULTIVALENT METAL COMPOUNDS, AND POLYMER ADHESIVE INTERPENETRATING NETWORK COMPOSITIONS AND METHODS

(75) Inventors: Venkat R. Garigapati, Southborough, MA (US); Brian J. Hess, Charlestown, MA (US); Cassandra L. Kimsey, Hoboken, NJ (US); Matthew E. Murphy, Whiterock Hill (IE)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 679 days.

This patent is subject to a terminal disclaimer.

(21) Appl. No.: 13/104,716

(22) Filed: May 10, 2011

(65) Prior Publication Data
US 2011/0277931 A1 Nov. 17, 2011

Related U.S. Application Data

(60) Provisional application No. 61/333,478, filed on May 11, 2010.

(51) Int. Cl.
*A61F 2/36* (2006.01)
*A61L 24/00* (2006.01)
*A61L 27/42* (2006.01)

(52) U.S. Cl.
CPC ........... *A61L 24/0068* (2013.01); *A61L 27/425* (2013.01)

(58) Field of Classification Search
CPC .... A61K 6/0023; A61K 6/0643; A61L 27/24; A61L 27/425; A61L 27/02
USPC .............. 156/331.6; 523/116, 117; 623/23.51
See application file for complete search history.

(56) References Cited

U.S. PATENT DOCUMENTS

| | | |
|---|---|---|
| 3,899,556 A | 8/1975 | Heide et al. |
| 4,183,915 A | 1/1980 | Gaffar et al. |
| 4,234,972 A | 11/1980 | Hench et al. |

(Continued)

FOREIGN PATENT DOCUMENTS

| | | |
|---|---|---|
| DE | 2620890 | 11/1977 |
| DE | 4216496 | 11/1993 |

(Continued)

OTHER PUBLICATIONS

Andriano, K.P. et al., "Preliminary In Vivo Studies on the Osteogenic Potential of Bone Morphogenetic Proteins Delivered from an Absorbable Puttylike Polymer Matrix," *J. Biomed. Mater Re (Appl. Biomater.)* 53:36-43 (2000). (8 pages).

(Continued)

*Primary Examiner* — Timothy Kennedy
(74) *Attorney, Agent, or Firm* — Lando & Anastasi LLP (57) ABSTRACT

Certain small molecule amino acid phosphate compounds such as phosphoserine and certain multivalent metal compounds such as calcium phosphate containing cements have been found to have improved properties and form an interpenetrating network in the presence of a polymer that contain either an electronegative carbonyl oxygen atom of the ester group or an electronegative nitrogen atom of the amine group as the bonding sites of the polymer surfaces to the available multivalent metal ions.

35 Claims, 2 Drawing Sheets

(56) References Cited

U.S. PATENT DOCUMENTS

| | | |
|---|---|---|
| 4,373,217 A | 2/1983 | Draenert |
| 4,491,987 A | 1/1985 | Park |
| 4,563,432 A | 1/1986 | Ehlert et al. |
| 4,563,489 A | 1/1986 | Urist |
| 4,596,574 A | 6/1986 | Urist |
| 4,600,546 A | 7/1986 | Grundei |
| 4,610,692 A | 9/1986 | Eitenmuller et al. |
| 4,629,464 A | 12/1986 | Takata et al. |
| 4,634,720 A | 1/1987 | Dorman et al. |
| 4,636,526 A | 1/1987 | Dorman et al. |
| 4,645,503 A | 2/1987 | Lin et al. |
| 4,654,314 A | 3/1987 | Takagi et al. |
| 4,661,536 A | 4/1987 | Dorman et al. |
| 4,672,032 A | 6/1987 | Slavkin et al. |
| 4,693,986 A | 9/1987 | Vit et al. |
| 4,713,076 A | 12/1987 | Draenert |
| 4,737,411 A | 4/1988 | Graves, Jr. et al. |
| 4,777,153 A | 10/1988 | Sonuparlak et al. |
| 4,781,721 A | 11/1988 | Grundei |
| 4,797,282 A | 1/1989 | Wahlig et al. |
| 4,798,585 A | 1/1989 | Inoue et al. |
| 4,839,215 A | 6/1989 | Starling et al. |
| 4,842,603 A | 6/1989 | Draenert |
| 4,846,838 A | 7/1989 | Takai et al. |
| 4,861,733 A | 8/1989 | White |
| 4,869,906 A | 9/1989 | Dingeldein et al. |
| 4,878,914 A | 11/1989 | Miwa et al. |
| RE33,161 E | 2/1990 | Brown et al. |
| 4,911,720 A | 3/1990 | Collier |
| RE33,221 E | 5/1990 | Brown et al. |
| 4,963,145 A | 10/1990 | Takagi et al. |
| 4,965,039 A | 10/1990 | Schuetz |
| 5,011,495 A | 4/1991 | Hollinger |
| 5,017,518 A | 5/1991 | Hirayama et al. |
| 5,030,396 A | 7/1991 | Saita et al. |
| 5,034,352 A | 7/1991 | Vit et al. |
| 5,053,212 A | 10/1991 | Constantz et al. |
| 5,055,307 A | 10/1991 | Tsuru et al. |
| 5,059,388 A | 10/1991 | Kihara et al. |
| 5,064,436 A | 11/1991 | Ogiso et al. |
| 5,089,195 A | 2/1992 | Ichitsuka et al. |
| 5,092,888 A | 3/1992 | Iwamoto et al. |
| 5,106,626 A | 4/1992 | Parsons et al. |
| 5,135,394 A | 8/1992 | Hakamatsuka et al. |
| 5,149,368 A | 9/1992 | Liu et al. |
| 5,152,791 A | 10/1992 | Hakamatsuka et al. |
| 5,171,720 A | 12/1992 | Kawakami |
| 5,207,710 A | 5/1993 | Chu et al. |
| 5,258,029 A | 11/1993 | Chu et al. |
| 5,263,985 A | 11/1993 | Bao et al. |
| 5,279,831 A | 1/1994 | Constantz et al. |
| 5,306,303 A | 4/1994 | Lynch |
| 5,318,779 A | 6/1994 | Hakamatsuka et al. |
| 5,338,356 A | 8/1994 | Hirano et al. |
| 5,338,772 A | 8/1994 | Bauer et al. |
| 5,385,887 A | 1/1995 | Yim et al. |
| 5,398,483 A | 3/1995 | Smith et al. |
| 5,409,982 A | 4/1995 | Imura et al. |
| 5,422,340 A | 6/1995 | Ammann et al. |
| 5,439,951 A | 8/1995 | Glimcher et al. |
| 5,464,440 A | 11/1995 | Johansson |
| 5,492,697 A | 2/1996 | Boyan et al. |
| 5,508,267 A | 4/1996 | Czernuszka et al. |
| 5,520,923 A | 5/1996 | Tjia et al. |
| RE35,267 E | 6/1996 | Tsuru et al. |
| 5,522,893 A | 6/1996 | Chow et al. |
| 5,522,894 A | 6/1996 | Draenert |
| 5,525,148 A | 6/1996 | Chow et al. |
| 5,531,794 A | 7/1996 | Takagi et al. |
| 5,536,575 A | 7/1996 | Imura et al. |
| 5,542,973 A | 8/1996 | Chow et al. |
| 5,545,254 A | 8/1996 | Chow et al. |
| 5,571,185 A | 11/1996 | Schug |
| 5,574,075 A | 11/1996 | Draenert |
| 5,597,897 A | 1/1997 | Ron et al. |
| 5,626,861 A | 5/1997 | Laurencin et al. |
| 5,641,502 A | 6/1997 | Skalla et al. |
| 5,650,108 A | 7/1997 | Nies et al. |
| 5,681,872 A | 10/1997 | Erbe |
| 5,695,729 A | 12/1997 | Chow et al. |
| 5,707,962 A | 1/1998 | Chen et al. |
| 5,717,006 A | 2/1998 | Daculsi et al. |
| 5,741,329 A | 4/1998 | Agrawal et al. |
| 5,766,618 A | 6/1998 | Laurencin et al. |
| 5,776,193 A | 7/1998 | Kwan et al. |
| 5,782,971 A | 7/1998 | Constantz et al. |
| 5,820,632 A | 10/1998 | Constantz et al. |
| 5,851,670 A | 12/1998 | Mitoh et al. |
| 5,866,155 A | 2/1999 | Laurencin et al. |
| 5,897,953 A | 4/1999 | Ogawa et al. |
| 5,914,121 A | 6/1999 | Robey et al. |
| 5,914,356 A | 6/1999 | Erbe |
| 5,922,025 A | 7/1999 | Hubbard |
| 5,939,388 A | 8/1999 | Rosen et al. |
| 5,962,427 A | 10/1999 | Goldstein et al. |
| 5,988,171 A | 11/1999 | Sohn et al. |
| 6,010,648 A | 1/2000 | Yamamoto et al. |
| 6,018,095 A | 1/2000 | Lerch et al. |
| 6,027,744 A | 2/2000 | Vacanti et al. |
| 6,030,635 A | 2/2000 | Gertzman et al. |
| 6,048,964 A | 4/2000 | Lee et al. |
| 6,051,247 A | 4/2000 | Hench et al. |
| 6,063,117 A | 5/2000 | Perry |
| 6,077,989 A | 6/2000 | Kandel et al. |
| 6,080,801 A | 6/2000 | Draenert et al. |
| 6,110,503 A | 8/2000 | Rickey et al. |
| 6,118,043 A | 9/2000 | Nies et al. |
| 6,129,928 A | 10/2000 | Sarangapani et al. |
| 6,136,029 A | 10/2000 | Johnson et al. |
| 6,165,486 A | 12/2000 | Marra et al. |
| 6,180,605 B1 | 1/2001 | Chen et al. |
| 6,180,606 B1 | 1/2001 | Chen et al. |
| 6,187,046 B1 | 2/2001 | Yamamoto et al. |
| 6,187,047 B1 | 2/2001 | Kwan et al. |
| 6,194,006 B1 | 2/2001 | Lyons et al. |
| 6,201,065 B1 | 3/2001 | Pathak et al. |
| 6,203,574 B1 | 3/2001 | Kawamura |
| 6,210,612 B1 | 4/2001 | Pickrell et al. |
| 6,235,225 B1 | 5/2001 | Okada et al. |
| 6,235,665 B1 | 5/2001 | Pickrell et al. |
| 6,261,322 B1 | 7/2001 | Despres, III et al. |
| 6,280,478 B1 | 8/2001 | Richter et al. |
| 6,281,257 B1 | 8/2001 | Ma et al. |
| 6,287,341 B1 | 9/2001 | Lee et al. |
| 6,296,667 B1 | 10/2001 | Johnson et al. |
| 6,306,297 B1 | 10/2001 | Ichitsuka et al. |
| 6,316,091 B1 | 11/2001 | Richart et al. |
| 6,325,992 B1 | 12/2001 | Chow et al. |
| 6,331,312 B1 | 12/2001 | Lee et al. |
| 6,335,430 B1 | 1/2002 | Qvist |
| 6,340,648 B1 | 1/2002 | Imura et al. |
| 6,346,123 B1 | 2/2002 | McKay |
| 6,350,462 B1 | 2/2002 | Hakamatsuka et al. |
| 6,358,532 B2 | 3/2002 | Starling et al. |
| 6,376,573 B1 | 4/2002 | White et al. |
| 6,395,036 B1 | 5/2002 | Czernuszka et al. |
| 6,432,437 B1 | 8/2002 | Hubbard |
| 6,432,919 B1 | 8/2002 | Wang et al. |
| 6,451,059 B1 | 9/2002 | Janas et al. |
| 6,458,162 B1 | 10/2002 | Koblish et al. |
| 6,479,418 B2 | 11/2002 | Li et al. |
| 6,495,156 B2 | 12/2002 | Wenz et al. |
| 6,511,510 B1 | 1/2003 | De Bruijn et al. |
| 6,521,246 B2 | 2/2003 | Sapieszko et al. |
| 6,524,345 B1 | 2/2003 | Valimaa et al. |
| 6,527,810 B2 | 3/2003 | Johnson et al. |
| 6,533,821 B1 | 3/2003 | Lally |
| 6,540,784 B2 | 4/2003 | Barlow et al. |
| 6,547,866 B1 | 4/2003 | Edwards et al. |
| 6,585,992 B2 | 7/2003 | Edwards et al. |
| 6,589,590 B2 | 7/2003 | Czernuszka et al. |
| 6,592,787 B2 | 7/2003 | Pickrell et al. |
| 6,599,515 B1 | 7/2003 | Delmotte |
| 6,616,742 B2 | 9/2003 | Lin et al. |

(56) References Cited

U.S. PATENT DOCUMENTS

| | | |
|---|---|---|
| 6,667,049 B2 | 12/2003 | Janas et al. |
| 6,670,293 B2 | 12/2003 | Edwards et al. |
| 6,692,761 B2 | 2/2004 | Mahmood et al. |
| 6,696,073 B2 | 2/2004 | Boyce et al. |
| 6,709,744 B1 | 3/2004 | Day et al. |
| 6,790,233 B2 | 9/2004 | Brodke et al. |
| 6,793,725 B2 | 9/2004 | Chow et al. |
| 6,800,245 B1 | 10/2004 | Erbe et al. |
| 6,808,561 B2 | 10/2004 | Genge et al. |
| 6,808,585 B2 | 10/2004 | Boyce et al. |
| 6,863,899 B2 | 3/2005 | Koblish et al. |
| 6,949,251 B2 | 9/2005 | Dalal et al. |
| 6,955,716 B2 | 10/2005 | Xu et al. |
| 6,987,136 B2 | 1/2006 | Erbe et al. |
| 6,987,170 B1 | 1/2006 | Silverman et al. |
| 7,018,460 B2 | 3/2006 | Xu et al. |
| 7,037,304 B2 | 5/2006 | Lyles et al. |
| 7,045,125 B2 | 5/2006 | Erbe et al. |
| 7,066,999 B2 | 6/2006 | Lin et al. |
| 7,081,161 B2 | 7/2006 | Genge et al. |
| 7,091,260 B2 | 8/2006 | Kuehn |
| 7,122,057 B2 | 10/2006 | Beam et al. |
| 7,172,679 B2 | 2/2007 | McKay |
| 7,238,203 B2 | 7/2007 | Bagga et al. |
| 7,258,735 B2 | 8/2007 | Lin et al. |
| 7,270,705 B2 | 9/2007 | Lin et al. |
| 7,294,187 B2 | 11/2007 | Chow et al. |
| 7,303,646 B2 | 12/2007 | Qvist |
| 7,318,841 B2 | 1/2008 | Tofighi et al. |
| 7,357,941 B2 | 4/2008 | Dalal et al. |
| 7,390,498 B2 | 6/2008 | Dalal et al. |
| 7,407,542 B2 | 8/2008 | Lemaitre et al. |
| 7,416,602 B2 | 8/2008 | Murphy et al. |
| 7,473,312 B2 | 1/2009 | Barralet et al. |
| 7,494,950 B2 | 2/2009 | Armitage et al. |
| 7,514,248 B2 | 4/2009 | Gower et al. |
| 7,514,249 B2 | 4/2009 | Gower et al. |
| 7,527,687 B2 | 5/2009 | Genge et al. |
| 7,544,496 B2 | 6/2009 | Gower et al. |
| 7,547,449 B2 | 6/2009 | Gower et al. |
| 7,575,628 B2 | 8/2009 | Lu et al. |
| 7,589,133 B2 | 9/2009 | Pomrink |
| 7,619,016 B2 | 11/2009 | Dickens et al. |
| 7,628,851 B2 | 12/2009 | Armitage et al. |
| 7,632,878 B2 | 12/2009 | Xu et al. |
| 7,648,728 B2 | 1/2010 | Yamamoto et al. |
| 8,173,149 B2 | 5/2012 | Dalal et al. |
| 8,232,327 B2 | 7/2012 | Garigapati et al. |
| 8,273,803 B2 | 9/2012 | Garigapati et al. |
| 2001/0014667 A1 | 8/2001 | Chen et al. |
| 2001/0051815 A1 | 12/2001 | Esplin |
| 2002/0022885 A1 | 2/2002 | Ochi |
| 2002/0035402 A1 | 3/2002 | De Bruijn et al. |
| 2002/0082694 A1 | 6/2002 | McKay |
| 2002/0114795 A1 | 8/2002 | Thorne et al. |
| 2002/0115742 A1 | 8/2002 | Trieu et al. |
| 2002/0151466 A1 | 10/2002 | Hubbard et al. |
| 2002/0193883 A1 | 12/2002 | Wironen |
| 2003/0009235 A1 | 1/2003 | Manrique et al. |
| 2003/0031698 A1 | 2/2003 | Roeder et al. |
| 2003/0069638 A1 | 4/2003 | Barlow et al. |
| 2003/0152606 A1 | 8/2003 | Gerber |
| 2004/0002770 A1 | 1/2004 | King et al. |
| 2005/0217538 A1 | 10/2005 | Reinstorf et al. |
| 2006/0089646 A1 | 4/2006 | Bonutti |
| 2006/0096504 A1 | 5/2006 | Grover et al. |
| 2006/0263443 A1 | 11/2006 | Chow et al. |
| 2007/0092580 A1 | 4/2007 | Chow et al. |
| 2007/0092856 A1 | 4/2007 | Chow et al. |
| 2007/0221093 A1 | 9/2007 | Erdrich et al. |
| 2008/0009955 A1 | 1/2008 | Shimp et al. |
| 2008/0028992 A1 | 2/2008 | Lee et al. |
| 2008/0069852 A1 | 3/2008 | Shimp et al. |
| 2008/0095817 A1 | 4/2008 | Murphy |
| 2008/0187571 A1 | 8/2008 | Clineff et al. |
| 2008/0188945 A1 | 8/2008 | Boyce et al. |
| 2009/0028949 A1 | 1/2009 | Leonard et al. |
| 2009/0028960 A1 | 1/2009 | Leonard et al. |
| 2009/0158964 A1 | 6/2009 | Insley et al. |
| 2009/0220475 A1 | 9/2009 | Bohner et al. |
| 2009/0258966 A1 | 10/2009 | Hirayama et al. |
| 2010/0120923 A1 | 5/2010 | Stewart et al. |
| 2010/0129416 A1 | 5/2010 | Murphy et al. |
| 2010/0168798 A1 | 7/2010 | Clineff et al. |
| 2010/0305626 A1 | 12/2010 | Stewart et al. |
| 2011/0150963 A1 | 6/2011 | Clineff et al. |
| 2011/0151027 A1 | 6/2011 | Clineff et al. |
| 2011/0277931 A1 | 11/2011 | Garigapati et al. |
| 2011/0287067 A1 | 11/2011 | Stewart |
| 2012/0237568 A1 | 9/2012 | Murphy et al. |

FOREIGN PATENT DOCUMENTS

| | | |
|---|---|---|
| DE | 29922585 | 7/2000 |
| DE | 10063119 | 8/2001 |
| EP | 0 267 624 | 5/1988 |
| EP | 0 360 244 | 3/1990 |
| EP | 0 987 032 | 3/2000 |
| EP | 1 027 897 | 8/2000 |
| EP | 1 142 597 | 10/2001 |
| GB | 2078696 | 1/1982 |
| GB | 2 323 083 | 9/1998 |
| GB | 2 348 872 | 10/2000 |
| GB | 2354518 | 3/2001 |
| JP | 59101145 | 6/1984 |
| JP | 59131346 | 7/1984 |
| JP | 59171546 | 9/1984 |
| JP | 60142857 | 7/1985 |
| JP | 6141466 | 2/1986 |
| JP | 6145748 | 3/1986 |
| JP | 6168054 | 4/1986 |
| JP | 61127658 | 6/1986 |
| JP | 63046167 | 2/1988 |
| JP | 64-030572 | 2/1989 |
| JP | 1108143 | 4/1989 |
| JP | 1126977 | 5/1989 |
| JP | 1230412 | 9/1989 |
| JP | 3191963 | 8/1991 |
| JP | 364482 | 10/1991 |
| JP | 429630 | 5/1992 |
| JP | 5042168 | 2/1993 |
| JP | 526504 | 4/1993 |
| JP | 5208877 | 8/1993 |
| JP | 566909 | 9/1993 |
| JP | 5237178 | 9/1993 |
| JP | 5305134 | 11/1993 |
| JP | 588687 | 12/1993 |
| JP | 655219 | 7/1994 |
| JP | 6296676 | 10/1994 |
| JP | 6102582 | 12/1994 |
| JP | 07-023994 | 1/1995 |
| JP | 7291759 | 11/1995 |
| JP | 9030988 | 2/1997 |
| JP | 11-276468 | 10/1999 |
| JP | 2000-262608 | 9/2000 |
| JP | 2001-058885 | 3/2001 |
| JP | 3231135 | 9/2001 |
| WO | WO 86/01113 | 2/1986 |
| WO | WO 87/04110 | 7/1987 |
| WO | WO 87/07495 | 12/1987 |
| WO | WO 93/07835 | 4/1993 |
| WO | WO 93/15721 | 8/1993 |
| WO | WO 93/20859 | 10/1993 |
| WO | WO 94/15652 | 7/1994 |
| WO | WO 94/15653 | 7/1994 |
| WO | WO 95/21634 | 8/1995 |
| WO | WO 97/31661 | 9/1997 |
| WO | WO 97/45147 | 12/1997 |
| WO | WO 97/46178 | 12/1997 |
| WO | WO 98/38949 | 9/1998 |
| WO | WO 98/47485 | 10/1998 |
| WO | WO 99/16478 | 4/1999 |
| WO | WO 99/16479 | 4/1999 |
| WO | WO 99/20319 | 4/1999 |

(56) References Cited

FOREIGN PATENT DOCUMENTS

| | | |
|---|---|---|
| WO | WO 99/37246 | 7/1999 |
| WO | WO 00/18443 | 4/2000 |
| WO | WO 00/35511 | 6/2000 |
| WO | WO 00/45870 | 8/2000 |
| WO | WO 00/45871 | 8/2000 |
| WO | WO 00/50104 | 8/2000 |
| WO | WO 01/03709 | 1/2001 |
| WO | WO 01/13970 | 3/2001 |
| WO | WO 01/28603 | 4/2001 |
| WO | WO 01/29189 | 4/2001 |
| WO | WO 01/44141 | 6/2001 |
| WO | WO 01/54746 | 8/2001 |
| WO | WO 01/66163 | 9/2001 |
| WO | WO 02/11781 | 2/2002 |
| WO | WO 02/15881 | 2/2002 |

OTHER PUBLICATIONS

Benoit, M.-A. et al., "Antibiotic-Loaded Plaster of Paris Implants Coated With Poly Lactide-co-glycolide as a Controlled Release Delivery System for the Treatment of Bone Infections," *International Orthopaedics* 21(6):403-408 (1997). (6 pages).
Breitbart, A.S. et al., "Tricalcium Phosphate and Osteogenin: A Bioactive Onlay Bone Graft Substitute," *Plastic and Reconstructive Surgery* 96:699-708 (1995). (10 pages).
Bucholz, R.W. et al., "Hydroxyapatite and Tricalcium Phosphate Bone Graft Substitutes," *Orthopedic Clinics of North America* 18:323-334 (1987). (12 pages).
Chow, L.C., "Solubility of Calcium Phosphates," *Monogr Oral Sci. Basel. Karger* 18:94-111 (2001). (18 pages).
Eggli, P.S. et al., "Porous Hydroxyapatite and Tricalcium Phosphate Cylinders with Two Different Pore Size Ranges Implanted in the Cancellous Bone of Rabbits," *Clinical Orthopaedics and Related Research* 232:127-138 (1988). (12 pages).
Gerhart, T.N. et al., "In vitro Characterization and Biomechanical Optimization of a Biodegradable Particulate Composite Bone Cement," *Journal of Biomedical Materials Research* 22:1071-1082 (1988). (12 pages).
Gombotz, W.R. et at., "Stimulation of Bone Healing by Transforming Growth Factor-Beta$_1$ Released from Polymeric or Ceramic Implants," *Journal of Applied Biomaterials* 5(2):141-150 (1994). (10 pages).
Hutmacher, D.W., "Scaffolds in Tissue Engineering Bone and Cartilage," *Biomaterials* 21:2529-2543 (2000). (14 pages).
Laffargue, PH. et at., "Evaluation of Human Recombinant Bone Morphogenetic Protein-2-Loaded Tricalcium Phosphate Implants in Rabbits' Bone Defects," *Bone* 25:55S-58S (1999). (4 pages).
Metsger, D.S. et al., "Histomorphometric Analysis of Tricalcium Phosphate Ceramic Implanted Into Turkeys," *Bone* 14:243-248 (1993). (6 pages).
Nade, S. et at., "Osteogenesis After Bone and Bone Marrow Transplantation," *Clinical Orthopaedics and Related Research* 181: 255-263 (1983). (9 pages).
Nery, E.B. et al., "Tissue Response to Biphasic Calcium Phosphate Ceramic With Different Ratios of HA/βTCP in Periodontal Osseous Defects," *Journal of Periodontology* 63:729-735 (1992). (7 pages).
Ohgushi, H. et al., "Marrow Cell Induced Osteogenesis in Porous Hydroxyapatite and Tricalcium Phosphate: A Comparative Histomorphometric Study of Ectopic Bone Formation," *Journal of Biomedical Materials Research* 24:1563-1570 (1990). (8 pages).
Ohura, K. et at., "Healing of Segmental Bone Defects in Rats Induced by a β-TCP-MCPM Cement Combined with rhBMP-2," *Journal of Biomedical Materials Research* 44:168-175 (1999). (7 pages).
Soriano, I. et at., "Formulation of Calcium Phosphates/Poly (d,l-lactide) Blends Containing Gentamicin for Bone Implantation," *Journal of Controlled Release* 68:121-134 (2000). (14 pages).

Tancred, D.C. et at., "A Synthetic Bone Implant Macroscopically Identical to Cancellous Bone," *Biomaterials* 19:2303-2311 (1998). (9 pages).
Thoma, K. et al., "Biodegradable Controlled Release Implants Based on β-Tricalcium Phosphate Ceramic," *European Journal Pharmaceutics and Biopharmaceutics* 38:107-112 (1992). (6 pages).
Uchida, A. et at., "Bone Ingrowth into Three Different Porous Ceramics Implanted into the Tibia of Rats and Rabbits," *Journal of Orthopaedic Research* 3:65-77 (1985). (13 pages).
Uchida, A. et al., "The Use of Ceramics for Bone Replacement," *The Journal of Bone and Joint Surgery* 66-B:269-275 (1984). (7 pages).
Vaccaro, A.R., "The Role of the Osteoconductive Scaffold in Synthetic Bone Graft," *Orthopedics* 25(5):571-578 (2002). (8 pages).
White, E. et al., "Biomaterial Aspects of Interpore-200 Porous Hydroxyapatite," *Dental Clinics of North America* 30(1):49-67 (1986). (19 pages).
Hua, W. et al. "New Bone Formation in the in vivo Implantation of Bioceramics," Chinese Medical Journal, vol. 105, pp. 753-757 (1992) (5 pages).
Lange, T.A. et al. "Granular Tricalcium Phosphate in Large Cancellous Defects," Annals of Clinical and Laboratory Science, vol. 16, No. 6, pp. 467-472 (1986) (6 pages).
Zheng, Q. et al. "Artificial bone of Porous Tricalcium Phosphate Ceramics and Its Preliminary Clinical Application," Journal of Tongji Medical University, vol. 12, pp. 173-178 (1992) (6 pages).
A. Reinstorf et al., "Phosphoserine—a convenient compound for modification of calcium phosphate bone cement collagen composites," Journal of Materials Science: Materials in Medicine 15 (2004), pp. 451-455, 2004 Kluwer Academic Publishers, Dresden, Germany.
W. Schneiders et al., "Effect of modification of hydroxyapatite-collagen composites with sodium citrate, phosphoserine, phosphoserine-RGD-peptide and calcium carbonate on bone remodelling," Bone 40 (2007) pp. 1048-1059, Elsevier, Nov. 19, 2006, Dresden, Germany, ww.elsevier.com-locate-bone.
International Search Report for Application No. PCT/US2009/64135 dated Apr. 2, 2010.
Mai et al. "O-phospho-L-serine: A Modulator of Bone Healing in Calciumphosphate Cements" Biomedizinische Technik, vol. 53, Issue 5, p. 229-233 esp. abstract, Oct. 2008.
Ishikawa et al. "Behavior of a Calcium Phosphate Cement in Simulated Blood Plasma in Vitro" Dental Materials, vol. 10, Issue 1, pp. 26-32 esp. abstract, Jan. 1994.
Chow et al. "A Natural Bone Cement—A Laboratory Novelty Led to the Development of Revolutionary New Biomaterials" Journal of Research of the National Institute of Standards and Technology, vol. 106, No. 6, pp. 1029-1033, Nov. 2001.
Fujimura et al. "A bioactive bone cement containing Bis-GMA resin and A-W glass-ceramic as an augmentation graft material on mandibular bone" Clinical Oral Implants Research, vol. 14, Issue 5, pp. 659-667 esp. abstract, Oct. 2003.
Bundy et al. "The Effect of Surface Preparation on Metal/Bone Cement Interfacial Strength" Journal of Biomedical Materials Research, vol. 21, Issue 6, pp. 773-805 esp. abstract, Jun. 1987.
Clarke "Role of Ceramic Implants, Design and Clinical Success With Total Hip Prosthetic Ceramic-to-Ceramic Bearings" Clinical Orthopaedics and Related Research, vol. 282, pp. 19-30 esp. abstract, Sep. 1992.
International Preliminary Report on Patentability for Application No. PCT/US2009/64135 dated May 26, 2011.
International Search Report and Written Opinion, dated Feb. 21, 2012, International Application No. PCT/US2011/060956, Applicant Howmedica Osteonics Corp. (13 pages).
(Vo-Dinh) Nanotechnology in Biology and Medicine, CRC Press (Jan. 24, 2007) [retrieved on Feb. 8, 2012] entire document retrieved from the Internet: <URL:http://books.google.com/books/aboutNanotechnology_in_biology_and_medicine.html?id=t9lPt1Hu6bAC>, (1 page).
International Search Report and Written Opinion dated Feb. 21, 2012, International Application No. PCT/US2011/060956, Applicant Howmedica Osteonics Corp. (13 pages).

FIG. 1

ORGANOPHOSPHOROUS, MULTIVALENT METAL COMPOUNDS, AND POLYMER ADHESIVE INTERPENETRATING NETWORK COMPOSITIONS AND METHODS

CROSS REFERENCE TO RELATED APPLICATIONS

The present application claims benefit of U.S. Provisional Application No. 61/333,478 filed May 11, 2010, the entire contents of which are incorporated herein by reference.

REFERENCE REGARDING FEDERALLY SPONSORED RESEARCH OR DEVELOPMENT

Not applicable

SEQUENTIAL LISTING

Not applicable

BACKGROUND OF THE DISCLOSURE

1. Field of the Disclosure

Improved calcium phosphate cements are well tolerated by the body. These improved cements include a non-covalently bonded interpenetrating network.

2. Description of the Background of the Disclosure

Calcium phosphate composites are used as bone substitutes and bone grafts. These calcium phosphate composites tend to form complexes primarily between calcium-based salts through charge interactions. These composites are used as general bone void fillers and generally lack the adhesive strength sufficient to adhere or fix bones together, for example, fractured surfaces. These prior compositions have insufficient chemical interaction between the calcium phosphate composite and the bone surface or other surface materials and lack sufficient strength to be used to attach bone to bone or bone to other materials.

Certain marine species, such as tubeworms and sand castle worms, rely on secreted proteins containing a high amount of the amino acid phosphoserine for adhesion mechanisms ("The tube cement of Phragmatopoma californica: a solid foam," Russell J. Stewart, James C. Weaver, Daniel E. Morse and J. Herbert Waite, Journal of Experimental Biology 207, 4727-4734, 2004). The specific mechanism of the phosphoserine involvement with the proteins is not understood; however, phosphoserine has been reported to be responsible for a specific interaction with calcium containing hydroxyapatite of bone as disclosed in U.S. Patent Application Publication No. 2005-0217538A1. In this publication, the authors mention calcium phosphate cements modified with phosphoserine (from 0.5% to 5% weight of the formulation) to aid as a compressive strength and surface area modifier in the bone cement material. In this range (from 0.5% to 5% weight of the formulation) the cement does not exhibit appreciable bone adhesion properties. In addition, certain bio-resorbable fibers have been used as adjuncts to calcium cements. These fibers include those based on polymers formed from mixtures of lactic and glycolic acids as well as other similar polymeric materials.

SUMMARY OF THE DISCLOSURE

One aspect of the present invention relates to a non-covalently bonded interpenetrating network that comprises a reactive mixture of a small amino acid phosphate species, a multivalent metal compound, and a polymeric material that contain functional groups that contains electronegative atoms as the bonding sites of the polymer surfaces to the available metal ions, in an aqueous environment.

A further aspect of the present invention relates to a bone restorative composition that comprises (i) a multivalent metal phosphate compound, (ii) a polymer that contain esters, carbonyl, carbonate, carboxylic acids, amides, amine groups and mixtures thereof as the bonding sites of the polymer surfaces to the available metal ions, (iii) a compound of the formula;

where A is O, $CH_2$, or S; R is H, $NH_2$, $NHCO(CH_2)_t CH_3$ where t is 0 to 2, $NH(CH_2)_x CH_3$ where x is 0 to 3, $NR1R2$ where R1 is $(CH_2)_y CH_3$ and R2 is $(CH_2)_y CH_3$ where y is 0 to 2, $(CH_2)_z CH_3$ where z is 0 to 3, where m is 0 to 1, and where n is 0 to 3 and wherein the compound is present in an amount greater than about 10% by weight based on the combined weight of the multivalent metal phosphate salt and the compound, and (iv) an aqueous medium.

A still further aspect of the present invention relates to kit for restoring bone comprising; A) A first container containing a composition that comprises: (i) a multivalent metal phosphate compound, (ii) a polymer that contain esters, carbonyl, carbonate, carboxylic acids, amides, amine groups and mixtures thereof as the bonding sites of the polymer surfaces to the available metal ions, and (iii) a compound of the formula;

where A is O, $CH_2$, or S; R is H, $NH_2$, $NHCO(CH_2)_t CH_3$ where t is 0 to 2, $NH(CH_2)_x CH_3$ where x is 0 to 3, $NR1R2$ where R1 is $(CH_2)_y CH_3$ and R2 is $(CH_2)_y CH_3$ where y is 0 to 2, $(CH_2)_z CH_3$ where z is 0 to 3, where m is 0 to 1, and where n is 0 to 3 and wherein the compound is present in an amount greater than about 10% by weight based on the combined weight of the multivalent metal phosphate compound and the compound, and B) a second container containing an aqueous medium.

Another aspect of the present invention relates to a method of adhering a material to a polymer comprising the steps of: placing a composition between the material and the polymer wherein the composition comprises (i) a multivalent metal phosphate compound, (ii) a compound of the formula;

where A is O, $CH_2$, or S; R is H, $NH_2$, $NHCO(CH_2)_t CH_3$ where t is 0 to 2, $NH(CH_2)_x CH_3$ where x is 0 to 3, $NR1R2$ where R1 is $(CH_2)_y CH_3$ and R2 is $(CH_2)_y CH_3$ where y is 0 to 2, $(CH_2)_z CH_3$ where z is 0 to 3, where m is 0 to 1, and where n is 0 to 3 and wherein the compound is present in an amount greater than about 10% by weight based on the combined weight of the multivalent metal phosphate salt and the compound, and (iii) an aqueous medium; and allowing the composition to cure to form an interpenetrating network at the interface between the composition and the polymer, wherein the polymer contain esters, carbonyl, carbonate, carboxylic acids, amides, amine groups and mixtures thereof as the bonding sites of the polymer surfaces to the available metal ions, and wherein the composition adheres to the material.

Other aspects and advantages of the present invention will become apparent upon consideration of the following detailed description.

DETAILED DESCRIPTION

Small molecule multivalent metal compounds such as calcium phosphates, including tetracalcium phosphate (TTCP) react with small molecule organophosphate compounds such as amino acid phosphate compounds like phosphoserine to form cements in the presence of aqueous environments that have cohesive and adhesive properties. When these cements are in the presence of polymer materials, the multivalent metal compounds and the amino acid phosphate compounds form a complex, interpenetrating network with the surface of polymer materials. The significance of these interpenetrating networks is the ability to form durable materials with high intrinsic strength (e.g. energy to failure) and in some cases extrinsic strength (e.g. adhesion to polymeric surfaces). The polymeric material added to the formulation to form high intrinsic strength can be in any form, such as solution, powder, fiber, resin, liquid crystal, hydrogel, chip, flake, sheet, mesh, and the like. The polymeric material to which the formulation can adhere can be in any form, such as plate, sheet, mesh, screw, pin, anchor, thread, fiber, suture, foam, film and the like. The complex formation of the interpenetrating network system involves several modes of ionic or ion-dipole interactions stemming from the release of multivalent metal ions such as calcium, magnesium, barium, strontium, and titanium ions and mixtures of these ions from compounds like calcium phosphate, magnesium phosphate, barium phosphates, strontium phosphate, titanium phosphate, zirconium phosphate, calcium oxide, magnesium oxide and mixtures thereof.

Certain small molecule amino acid phosphate compounds, such as phosphoserine, have a phosphate group ($PO_4$), a carboxyl group (COOH), and an amine group ($NH_2$) which are all capable of forming ionic interactions with the available metal ions. For rapid and abundant interactions, TTCP is the ideal metal ion source since it has the highest calcium to phosphate ratio (2:1) of the known calcium phosphate compounds and is well tolerated by the body. Basic TTCP is a calcium rich small molecule that is highly strained and dynamic. As it reacts in an acidic environment, the structure opens to release the calcium ions for ionic bonding. When it releases the calcium, the phosphoryl oxygen of the phosphate group of the TTCP intermediate is available for additional calcium ionic bonding. On this basis the authors hypothesize one method is to manufacture a calcium rich molecule with a calcium to phosphate higher then 2:1 which is even more reactive compared to TTCP. In addition, compositions with less reactivity can also be suitable for use. Such compositions could utilize calcium phosphate compounds with a calcium to phosphate ratio less than 2:1, such as alpha-tricalcium phosphate (1.5:1) or compositions could utilize calcium based compounds which are not from the calcium-phosphate family, such as calcium chloride or calcium oxide. It is preferred that the multivalent metal compound be non-toxic as many uses of these compositions are for medical and/or veterinary uses. However, if the cement is not to be used relative to living organisms, toxicity is of less concern. Suitable multivalent metal compounds include: calcium phosphate, magnesium phosphate, barium phosphates, strontium phosphate, titanium phosphate, zirconium phosphate, calcium oxide, magnesium oxide and mixtures thereof. In addition, non-phosphate compounds of these metals such as carbonates, bicarbonates, sulfates and nitrates can replace some or all of the above phosphate compounds.

Figure 1:
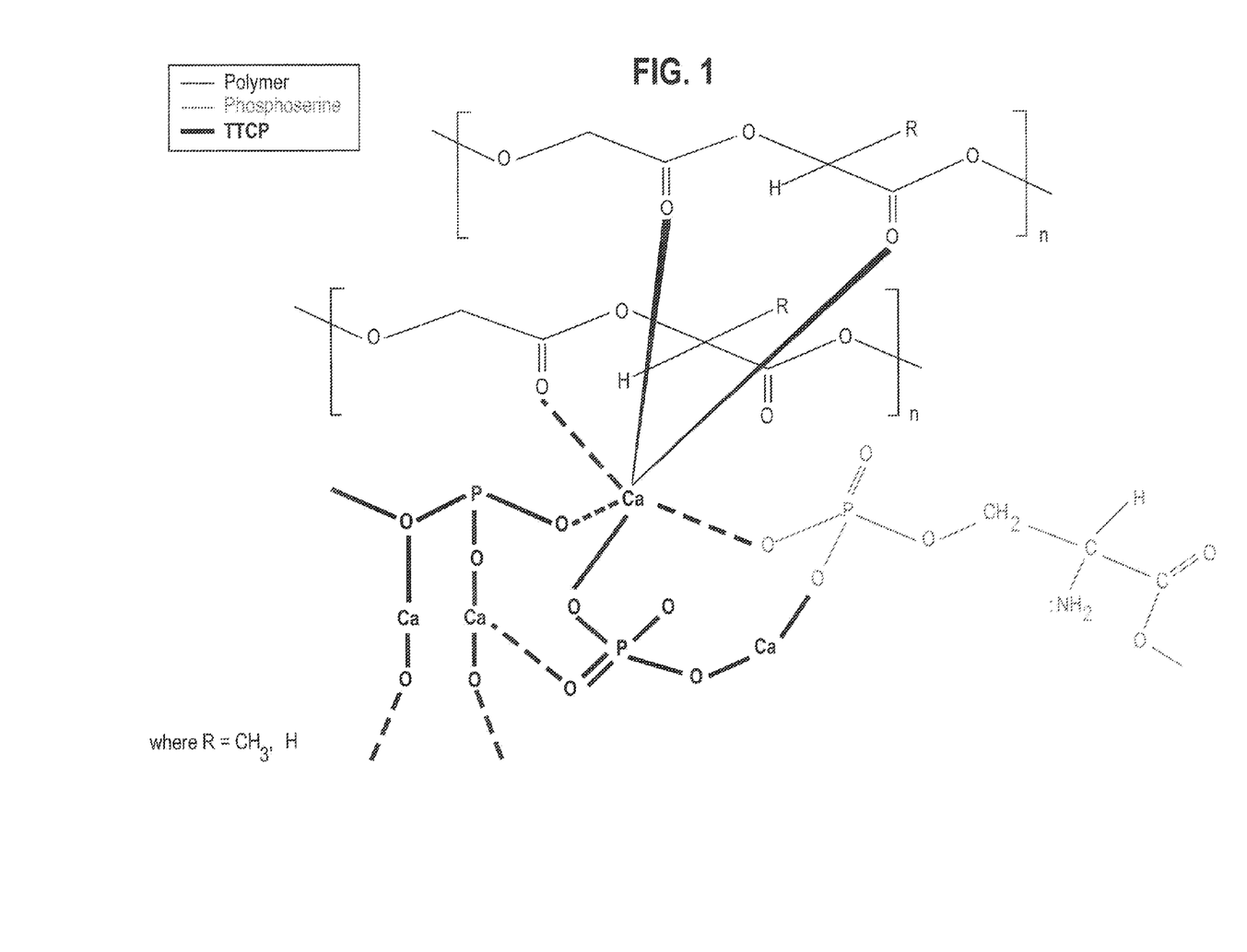
FIG. 1 is a diagram showing detail of a proposed structure of the interpenetrating network of the present disclosure.

To establish a fully integrated interpenetrating network system, ion-dipole multivalent metal ion interactions develop and are extended to the polymer surfaces. For example, with TTCP and phosphoserine, the electronegative carbonyl oxygen atom(s) of the ester group or the electronegative nitrogen atom(s) of the amine group are the bonding sites of the polymer surfaces to the available calcium ions. The reactive and charged TTCP/phosphoserine complex that develops influences the folding of the adjacent polymer chains on the polymer surface in a favorable geometry to enhance the ion-dipole bonding. In addition, both the hydrophobicity and steric structure of the polymer backbone influences the degree of interaction between the polymer to the TTCP/phosphoserine complex. This geometry is depicted in FIG. 1. The structure of FIG. 1 has been confirmed based on solid state NMR ($^{13}C$, $^{15}N$ and $^{31}P$) and FT-IR analysis. Solid state NMR data suggest that the $-NH_2$, $-COOH$ and $-P(O)(OH)_2$ groups of phosphoserine are involved in a reaction with the calcium ions of TTCP to form a hybrid organic/inorganic macromolecular network through calcium ion bridges. The incorporation of PLGA fibers or polymer surfaces interact with the reactive species which are generated from TTCP and phosphoserine and result in the formation of an interpenetrating network onto the polymer surface. Electronegative carbonyl moiety (ester function) of PLGA involve in reaction with reactive TTCP/phosphoserine to form calcium bridges through ionic interactions. Thus the fibers augment the strength of the TTCP and phosphoserine system by participating in the formation of an interpenetrating polymer network which is quite distinctive from the current fiber reinforced calcium-based bone cements which are currently on the market. In this analysis, the FT-IR analysis also showed that in a mixture of dry TTCP, phosphoserine and polymer, that there were no bands showing an interaction amongst these components in the dry state. However, when an aqueous solution was added, e.g. water, within 30 seconds there were strong shifts in the spectrum showing a reaction among the TTCP, phosphoserine and the polymer consistent with the structure shown in FIG. 1. Based on the NMR and FT-IR data, the TTCP and phosphoserine react rapidly in water to form a macromolecular network with the polymer through calcium bridges and hydrogen bonding. Calcium phosphate cements without sufficient organophosphates such as phosphoserine do not have as much ability to influence this polymer folding effect; thus the ion-dipole interaction is not as strong and gives inferior intrinsic or extrinsic strength. One calcium ion in the interpenetrating network system has the ability to interact with more than one electronegative carbonyl oxygen or electronegative nitrogen group from the polymer surface. An example of this ion-dipole interaction is with the calcium ion and the ester moiety of hydroxybutyrate polymer to from a coordinate complex [Rosetta Natoli Reusch and Harold L. Sadoff, Putative structure and functions of a poly-β-hydroxybutyrate/calcium polyphosphate channel in bacterial plasma membranes, Proc. Nat. Acad. Sci. USA, Vol. 85 [June 1988] p. 4176-4180].

It has further been found that certain multivalent metal compound cements that include a certain minimum amount of small amino acid phosphate compounds of the formula;

where A is O, $CH_2$, or S; R is H, $NH_2$, $NHCO(CH_2)_tCH_3$ where t is 0 to 2, $NH(CH_2)_xCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3 have superior strength in the presence of polymeric compounds that have ionically available electron pairs compared to known calcium phosphate or multivalent metal compound cements. Preferred adjunct compounds are those where A is O or $CH_2$, R is H or $NH_2$, m is 0 or 1 and n is 0 or 1. It is also possible that other similar materials that can assist the multivalent metal ionically bond to reactive sites on the resorbable polymer materials are usable in the calcium phosphate mixture. At present one preferred species is phosphoserine.

The compositions as described herein are useful in a wide variety of medical applications. One use of the compositions is to adhere bone fragments together within the body. This is useful, for example, during surgery to allow for temporary fixation prior to definitive hardware placement, and to enhance fracture fixation by adhering both load and non-load bone fragments together alone and/or in the presence of appropriate immobilization. The compositions also enhance screw and/or bone anchor fixation into low density cancellous bone at and/or after surgery, to allow screw fixation when the core diameter of the screw hole is larger then the screw major diameter, for instance to reattach a metal or bioresorbable screws to bone that has stripped from the surrounding material, to adhere a metal or bioresorbable plate to fractured bones allowing for reduction and/or elimination of metal or bioresorbable screws or pins used to fix a metal or bioresorbable plate to bone. The use of the compositions with a bioresorbable suture may be used to help fixate small bones after fracture. The compositions also have the capacity to enhance fixation of a joint replacement prosthesis to bone (e.g. hip acetabular cup or femoral stem). The compositions adhere the junction of at least one of a tendon, ligament, cartilage, a bone graft, and/or dental implants to bone. The compositions may be used to support new bone growth for dental socket or dental ridge augmentation. The compositions have the capacity to adhere to bony defect perimeters while filling gaps creating a seal to prevent leakage (e.g. cerebral spinal fluid). Furthermore, the compositions may also be used in ossicular chain reconstruction to adhere middle ear ossicles together. The adhesive properties of the compositions of the present invention to bone and bone to other materials make them useful to provide bony contour for facial bone augmentation applications. These compositions are also useful for gluing cancellous bones, cortical bones and a combination of both, whether in fatty or greasy environments potentially without any surface pretreatment prior to application.

One particularly novel use of the compositions is as a bone restorative composition. By a bone restorative composition, it is meant a composition that is useful to restore and/or repair bone, such as bone adhesives, bone cements, bone glues, bone putties, bone void fillers, bone replacement compositions, cements and/or adhesives to fix screws, metal or bioresorbable implants and at least one of a tendon, ligament, cartilage, a bone graft, and/or a dental implants to bone.

As noted above, the compositions have a tacky state shortly after initial mixing. This tacky state enables at least two items, such as two pieces of bone, bone and another material, or two non-bone materials to be held together by the composition itself, without the need for external force, until the composition sets to the final hardened cement state. The amount of force needed to remove two opposed pieces of material from each other is the separation strength. For the composition as described herein, these compositions have a separation strength during the tacky state within the first 4 minutes and preferably within the first 2 minutes after initial mixing from about 10 kPa to about 250 kPa and preferably from about 50 kPa to about 150 kPa. For certain applications it may be useful to have a longer tack state whereby certain compositions have a separation strength which continues in this range for up to 12 minutes. This separation strength is sufficiently high that the items to be joined need not be held together unless there is an apposing strength of the items greater than the separation strength and also, the items can still be repositioned or even reapposed without loss of ultimate bond strength.

It has been found that in the present compositions tetra calcium phosphate (TTCP) has unusual properties not shared by other calcium phosphate compositions or other multivalent metal compounds. TTCP is the most basic of all the calcium phosphates; therefore, it readily reacts to acidic compounds. While other calcium phosphate compositions can be used in addition to the TTCP, it is preferred that the compositions include an effective amount of TTCP. The TTCP used in the present compositions can be made by a variety of methods. One such manufacturing method is disclosed by Chow and Takagi in U.S. Pat. No. 6,325,992, the disclosure of which is hereby incorporated by reference. The TTCP can be 100% pure material or can include other calcium and calcium phosphate materials as an impurity, e.g. α-TCP, CaO and/or HA.

Typical amounts of multivalent metal compounds are from about 10% to about 89.9% by weight based on the total composition of the dry ingredients, namely the metal compound, the small amino acid phosphate species and the polymer. A preferred and optimum amount of the divalent metal compound is from about 40% to about 80% and about 55% to about 65% by weight on the same basis.

A second component of the compositions is a small amino acid phosphate species that has the following formula;

where A is O, $CH_2$, or S; R is H, $NH_2$, $NHCO(CH_2)_tCH_3$ where t is 0 to 2, $NH(CH_2)_xCH_3$ where x is 0 to 3, NR1R2 where R1 is $(CH_2)_yCH_3$ and R2 is $(CH_2)_yCH_3$ where y is 0 to 2, $(CH_2)_zCH_3$ where z is 0 to 3, where m is 0 to 1, and where n is 0 to 3. Preferred compounds are those where A is O or $CH_2$, R is H or $NH_2$, m is 0 or 1 and n is 0 or 1.

The most preferred small amino acid phosphate species is phosphoserine that has the following structure;

The compounds that are structurally similar to phosphoserine, which contain the reactive phosphonate or phosphate, and which have COOH functional groups, are capable of interacting with the $Ca^{++}$ within the TTCP to form a calcium based matrix and are referred to as compounds structurally similar to phosphoserine in this description. The combination of these functional groups plus the geometry properties of the matrix such as the chain length between the phosphorous and the COOH are unique aspects to the molecules which affect the level of adhesive bonding strength to substrate surfaces such as bone and metal.

The preferred compound that is structurally similar to phosphoserine is any form of phosphoserine, including the phospho-D-serine, phospho-L-serine or the phospho-DL-serine, and/or other similarly constructed compounds. The exact stereochemistry of the phosphoserine does not seem to have any impact on the properties of the compositions disclosed herein.

It has been found that when the quantity of the small amino acid phosphate species are included in the mixture and are increased beyond about 10% w/w based on the total composition of the dry ingredients, namely the metal compound, the small amino acid phosphate species and the polymer, more generally in the range of about 10% to about 89.9%, more typically in the range of about 15% to about 50%, or preferably from about 20% to about 40%, the tack and adhesion properties of the resulting compositions were significant. At such levels, the influence of the small amino acid phosphate species extends beyond internal interaction with the cement, but also extends to significant binding with the hydroxyapatite architecture and proteins of bone. At below about 10% by weight of the small amino acid phosphate species, the compositions do not have a tacky state and these compositions do not have adhesive properties.

Factors that may affect the length of the tacky state, the length of the putty states and the ultimate cure time, as well as strength properties of the compositions include: the percentage (w/w) multivalent metal compound and the small amino acid phosphate species based solely on the weight of the multivalent metal compound and the small amino acid phosphate species in the composition, the selection of the small amino acid phosphate species, the particle size of the multivalent metal compound, and the nature and quantity of any additives and/of fillers which may be combined to the composition to enhance the material properties.

The mean particle size of the multivalent metal compound should be below about 1000 µm, preferably about 1-250 µm, most preferably about 10-100 µm. As the mean particle size of the multivalent metal compound is reduced, the multivalent metal compound tends to dissolve too fast and these compositions may not be practical for all uses as disclosed herein. On the other hand if the multivalent metal compound has a mean particle size of greater than about 1000 µm, the intra-operative performance of the compositions may not have the desired initial strength and be too slow to set. If a longer working time is desired, then multivalent metal compound with a larger mean particle size can be used; however, if a shorter working time is desired, then multivalent metal compound with a smaller mean particle sizes can be used. In certain use environments, compositions that have a multi-modal mean particle size distribution with, for example, one mode less then about 50 µm and the other mode above about 50 µm can provide unique properties such as a fast initial cure rate from the smaller mean particle size mode combined with higher intrinsic compression strength of the material from the larger mean particle size mode.

The aqueous based mixing media useful for combining the multivalent metal compound and the small amino acid phosphate species powders can include water, buffers such as sodium phosphate, saline, and blood based products such as whole blood, plasma, platelet rich plasma, serum, and/or bone marrow aspirate. The blood based products are used with the goal of achieving enhanced rate of bone healing and remodeling. It is also possible to use the compositions without premixing with an aqueous medium if the composition is to be used in a sufficiently wet environment that the aqueous medium can be absorbed from the in situ site. In this situation, the composition can be dusted on and/or other wise applied to the desired site and then mixed with the liquids that are already present at the site. The amount of aqueous medium is not particularly important other than the amount should be chosen to provide the consistency of the desired product for use as a bone restoration composition or other use.

Suitable polymers must contain functional groups that contains electronegative atoms as the bonding sites of the polymer surfaces to the available metal ions, such as electronegative carbonyl oxygen atom(s) of the ester group or electronegative nitrogen atom(s) of the amine group as the bonding sites of the polymer surfaces to the available calcium ions. These functional groups can be either in the backbone chain of the polymer or in groups that are pendant to the polymer chain. These polymeric based compounds can include, but are not limited to, one or more of the following; poly(L-lactide), poly(D,L-lactide), polyglycolide, poly(ε-caprolactone), poly(teramethylglycolic-acid), poly(dioxanone), poly(hydroxybutyrate), poly(hydroxyvalerate), poly(L-lactide-co-glycolide), poly(glycolide-co-trimethylene-carbonate), poly(glycolide-co-caprolactone), poly(glycolide-co-dioxanone-co-trimethylene-carbonate), poly(tetramethylglycolic-acid-co-dioxanone-co-trimethylene-carbonate), poly(glycolide-co-caprolactone-co-L-lactide-co-trimethylene-carbonate), poly(hydroxybutyrate-co-hydroxyvalerate), poly(methyl-methacrylate), poly(acrylate), polyamines, polyamines, polyimidazoles, poly(vinyl-pyrrolidone), collagen, silk, chitosan, hyaluronic acid, gelatin and mixtures thereof. In addition, copolymers of the above homopolymers also can be used. The general structural nature of polymers include linear homo and copolymers, cross linked polymers, block polymers, branched and hyper branched polymers and star shaped polymers. The polymers can be added to the formulation in the form of a solution, powder, fiber, resin, liquid crystal, hydrogel, chip, flake, and the like. The polymeric material can be included directly within the cement formulation or can be an adjunct that is applied in situ as the cement is applied to the bone. The only import aspect is that sufficient polymeric material is available to ionically bond with the calcium phosphate and the adjunct material as described below.

The polymeric material can that is included within the composition should be sufficient to show a difference in intrinsic material strength (e.g. the bending moment energy to failure). That amount should be of sufficient weight within the formulation; amounts greater than about 0.1% w/w based on the total weight of the dry components of the composition would be sufficient. The polymeric material included within the composition can be up to about 30% w/w based on the total weight of the dry components of the composition; however, as such levels the adhesive properties decrease; therefore, a balance between intrinsic strength and material adhesive properties is required. For polymeric materials in contact with the composition it is important that the surface area of the polymer is readily available at the molecular level or is in direct contact with the composition.

It has been confirmed as noted above that the polymers form an interpenetrating network having a structure similar to what is shown in FIG. 1. In the illustrated network, the calcium ions from the TTCP form a non-covalently bond, such as an ionic bond, with the phosphoryl oxygen of the TTCP and the phosphoserine and also form ion-dipole bonds with the oxygen atoms in both the backbone of the polymer and pendant to the polymer backbone. The polymer molecules shown in FIG. 1 could represent either the molecules from the surface of a polymer such as from a fiber added intrinsically to the composition or a molecule from the surface of an extrinsic polymer source such as a bioresorbable polymeric based plate.

The interpenetrating networks can be formed at both an acidic and a basic pH. However, only when the pH is raised to a level above pH of about 5 and preferably above a pH of about 6 so the interpenetrating networks form permanent bonds. Also the pH should typically be below a pH of about 9 to be tolerated by the body. If the materials are to be used for other purposes, there is no upper limit other than a pH that will degrade the polymeric material.

Additives may be included in the compositions disclosed herein to further enhance the material properties. These properties include the handling, porosity, intrinsic material strength, & bone healing rate (osteogenic). Depending on the multivalent metal compound chosen, suitable additives might include: alpha or beta tri-calcium phosphate ($\alpha$-TCP or $\beta$-TCP), calcium sulfate, calcium silicate, calcium carbonate, sodium bicarbonate, sodium chloride, potassium chloride glycerol phosphate disodium, amino acids such as serine, excess amounts of phosphoserine, polyols (such as glycerol, mannitol, sorbitol, trehalose, lactose, & sucrose), silk, keratin (primarily found in human hair), autologous bone powder or chips, demineralized bone powder or chips, collagen, BMP7, stem cells, parathyroid hormone (PTH), bisphosphonates, and mixtures thereof. In addition, other additives and/or fillers could be incorporated which offer surgical visual aids & anti-infective properties.

The $\alpha$-TCP and $\beta$-TCP additive component typically is also in granular form. The granules presently contemplated have an overall diameter size in the range of about 0.1 to about 2 mm, or preferably between about 0.5 to about 0.1 mm. Larger and smaller granules can be used depending on the other components of the composition and the desired end properties. In the present compositions, the particle size of the granules has an impact on the mechanical strengths of the resultant compositions. The total porosity of these granules is in the range of about 40-80%, more preferably about 65-75%, and the average pore diameter size of the granules in these compositions is in the range of about 20-500 µm, preferably about 50-125 µm. The granules do not dissolve within the present embodiments during the curing phase, but interact as a solid particle with the other components of the compositions. In the present compositions, the porosity and pore size listed here has an impact on the resorption characteristics of the resultant compositions and to allow for bony in growth and healing as described by Dalal et al. in U.S. Pat. No. 6,949,251.

The additives that affect the porosity include cement curing pore forming agents such as calcium carbonate or sodium bicarbonate, granules with pre-formed pores made from alpha or beta tri-calcium phosphate ($\alpha$-TCP or $\beta$-TCP), biodegradable polymers usually in fiber form that open channels or pores as they degrade relatively quick in vivo such as PGA, or copolymers such as PLGA, or biodegradable fibers that open channels or pores as they degrade over relatively long time periods such as PLLA, silk, keratin, collagen, autologous bone powder or chips, or demineralized bone powder or chips. The rate at which the biodegradable polymers degrade can be dependant on the physical state of the crystalline structure when processing the polymer. Amorphous polymers may resorb faster than crystalline polymers. Other biodegradable polymers not in the form of fibers, rather powders, can be used such as PLLA, PGA, PLGA, PEG, or block polymers such as PLLA-PEG-PLLA. Small molecules may also be used which leach away relatively quickly from the cement as it cures; for example, these materials may include sodium chloride, potassium chloride, glycerol phosphate disodium, polyols (such as glycerol, mannitol, sorbitol, trehalose, lactose, & sucrose), amino acids such as serine, and/or excess amounts of phosphoserine. Other materials that form pores may dissolve or resorb over time in vivo and release from the cement opening pores; these materials include calcium sulfate, $\alpha$-TCP or $\beta$-TCP powder or granules. Granules can be used to alter the in vivo resorption profile, such as $\alpha$-TCP or $\beta$-TCP granules, or hybrid granules made from calcium sulfate and $\alpha$-TCP or $\beta$-TCP in which the calcium sulfate portion resorbs more quickly.

The additives that affect the bone healing rate driven by new bone ingrowth can be influenced by the level of porosity of the cured cement. This rate can be manipulated by the number of pores and size of the pores created within the cured cement. Achieving such porosity up to about 60% v/v was demonstrated by controlling the ratio of composition ingredients. The porosity that develops during the curing process can be controlled by the amount of pore forming agent added (such as calcium carbonate), the level of compound structurally similar to phosphoserine added, the level of aqueous solution used, and/or the level of other agents added to the composition. Increasing the porosity reduces the material intrinsic strength; however, a balance of porosity vs. strength is critical for achieving the clinical application. Additives that increase the intrinsic material strength can be incorporated to offset the loss of strength by creating porosity.

These polymeric materials can be supplied as fibers into the composition to increase the material intrinsic strength. An important aspect for chemical ion-dipole adhesion of these fibers is the size and/or surface area. The size or surface area can be defined by the aspect ratio (length:diameter). The preferred aspect ratio is from 2:1 to 50:1; more preferable from 10:1 to 35:1. The overall length of the fiber can be up to 5 mm; however, since the material could be used as bone to bone adhesive, the length of the fiber may be more appropriate at lengths up to 2 mm.

The additives that act as visual aids in the surgical procedure include colorants such as a pigment or dye to aid in determining coverage and depth of the applied cement or contrast agents such as barium salts in determining depth on a radiograph.

Other additives can be incorporated into the compositions that enhance the bone healing rate (osteogenic) These additives comprise a class of osteogenic growth factors including bone morphogenetic proteins (BMP's), such as BMP 7, stem cells, parathyroid hormone (PTH) and/or anti-osteoporotic agents such as bisphosphonates can be contemplated for incorporation into the composition.

Other additives that can be incorporated into the composition are infection preventatives such as broad spectrum antibiotics and anti-infectic additives.

The compositions as described herein have many unique properties not found in prior calcium phosphate compositions. One particularly important property is that the compositions have a tacky state immediately subsequent to mixing with an aqueous medium. This tack property is retained for a number of minutes, sometimes up to about 12 minutes depending on the application requirement, typically up to about 4 minutes, and preferably up to about 2 minutes, after mixing with the aqueous medium. The time of the tacky state is dependent on a number of factors including relative ratio of the components, the particle sizes of the component materials, the presence of additives and the like. During this time the compositions will adhere bone to bone and bone to other materials, often without the need for external clamping or other application of pressure. The tacky state is not so aggressive that the composition will permanently affix the materials together at this point in time. Rather the tacky state can allow the materials to be moved relative to each other and also to be re-opposed without appreciable loss of ultimate cured strength. This is important in a medical setting so that the user can make sure the bone and the other material to be adhered to the bone are in the proper position relative to each other.

The tacky state is followed by a putty state. In the putty state, the tacky property has substantially disappeared and the compositions can be shaped or sculpted. In addition, during the putty state, the composition can be formed into shapes or used to fill voids in bone in a manner similar to putty. This putty state is retained for a number of minutes, sometimes up to 15 minutes depending on the application requirement, typically up to about 8 minutes, and preferably up to about 5 minutes, after mixing with the aqueous medium. Like the tacky states, the putty state is dependant on a number of factors including the relative ratio of the components, the presence of additives, the particle size of the components and the like. Because the items to be affixed can be repositioned during the tacky state or the compositions can be shaped during the putty state, this combined time of the tacky state and the putty state is some times referred to as the working time. Typical compositions have a working time of up to about 8 minutes from initial mixing and often the working time is up to about 5 minutes after which time the compositions have sufficiently begun hardening that further manipulation will result in degradation of ultimate strength of the bond.

After the putty state, the compositions harden like a cement to form a substantially permanent bond between the materials. In the cement state, the composition hardens and the materials that have been affixed to each other cannot be separated without the application of significant force. The compositions typically will begin to harden within about 8 minutes, and often within about 5 minutes, after mixing with the aqueous medium. The amount of time to reach the cement state is also dependant of the same factors listed above.

A further important property of the compositions is that these compositions have significant coherency and integrity within a wet environment. In the medical field, this would include a surgical site and a wound or similar situation where blood and other bodily fluids are present. The tacky state, the putty state, and the cement state all occur in either a wet environment or in a dry environment. In order to get the desirable properties, the user need not ensure that the application site is clean and dry. In a wet environment, the compositions tend to remain together and the presence of the liquid does not significantly affect the integrity of the composition or the ultimate strength properties.

While not wishing to be bound by theory, compositions of the present disclosure are believed to function as follows: the TTCP, which is basic in nature, reacts with the small amino acid phosphate species, which is acidic in nature, upon mixing with the aqueous medium and forms a hardened, layered structure upon curing. This reaction is exothermic; the degree of exothermic activity depends on a number of factors including the volume of the composition. The low pH nature of the compounds that are structurally similar to phosphoserine enable the hydroxyl of phosphate or phosphonate and COOH functional group to bond through ionic interaction with the calcium ions from within the TTCP. This resulting reactive intermediate continues a cascade of ionic interactions with calcium and phosphate ions within the TTCP or HA on the bone surface or any other metal ions of the metal implants. This series of interactions provides transient material having the tacky properties while curing and the adhesion strength that increases upon cure.

The exothermic properties of the composition when curing are prevalent when mixing as a large volume bone void filler (usually greater then 10 cc) and this may serve as an effective means to kill the residual tumor cells locally that remain after surgical bone tumor removal.

The exothermic properties of the composition may lead to necrosis of local tissue and this also reduces the adhesive working time. The amount of heat released by the exothermic reaction is mainly influenced by the volume of the composition, the size of the particles and the ratio of compound that is structurally similar to phosphoserine to TTCP. With larger volumes of composition, more heat is released to the surrounding tissue. With volumes less than or equal to about 1 cc, the heat release is negligible with maximum temperature reached during the curing of the adhesive being below about 40° C. The higher volume compositions greater than about 1 cc, led to considerable heat release, even exceeding about 60° C. in compositions greater than about 5 cc. To manage this exothermic heat release to below about 45° C., the particle size distribution of the TTCP, and the ratio of TTCP to compound that is structurally similar to phosphoserine can be chosen appropriately. The smaller TTCP particles dissolve and react faster due to a higher specific surface area; therefore, to reduce the exothermic heat release, the composition can be adjusted by choosing a TTCP particle size distribution which generally has a mean particle size greater than about 15 µm, more specifically about 25 µm. In addition, the greater amount of TTCP to the compound that is structurally similar to phosphoserine used, the faster the reaction occurs due to the number of calcium ions available for bonding. Exothermic heat release can be limited by adding more compound that is structurally similar to phosphoserine to the composition. To further reduce the exothermic heat release, endothermic additives can be incorporated into the composition to slow the reaction rate; these include polyols (such as sorbitol or mannitol) and/or PEG. The factors discussed here can be chosen to design several compositions; all of which have exothermic profiles which limit or eliminate necrotic reactions to local tissues while tailoring the compositions with sufficient working time for the clinical application.

The compositions when mixed with aqueous medium typically have a creamy or a tacky paste consistency initially.

Also, the mixing of the compositions with the aqueous medium does not require a high level of force or shear. Generally, simple hand mixing, such as with a spatula, is sufficient in most instances. It is envisioned that the present compositions may be applied via injection through a syringe or other suitable pressurized implement, applied with a spatula, and as otherwise desirable by a user. The creamy or tacky viscosity allows for application of the composition to the defect site for a defined period of time. The compositions allow the bone to be repositioned several times within about 4 minutes and preferably within about 2 minutes without losing tack properties. If the compositions need to be injected through a syringe or cannula, the viscosity of the composition during the working time can be important. For these situations, viscosities of the compositions herein should be preferably below about 150 centipoise.

Still further embodiments have a consistency similar to putty. These embodiments are useful for filling larger defects, have sculpting properties, or for mechanical interlocking into cancellous bone. These compositions hold their cohesive, tacky, and sculpting properties over a longer period of time even when subjected to a wet field. The compositions have working time for sculpting sometimes up to about 15 minutes depending on the application requirement, typically up to about 8 minutes, and preferably up to about 5 minutes, after mixing with the aqueous medium. Formulations with an increased amount of small amino acid phosphate species greater than about 25% w/w or increased TTCP mean particle size greater than about 250 microns tend to have longer working times and seem to be suitable for use in situations were the putty will fill defects in structures that are well supported by surrounding bone. In these situations the putty does not need to harden as fast provided it maintains its cohesive properties in the wet field. Another property of the compositions is that the compositions will adhere to themselves as well as to an external surface such as bone. This is useful in situations where a shape is formed during the putty state and this shape can then adhere to bone. Also, in some instances a user may apply a mass of the composition to a bone or other surface and then shape the composition into the final desired shape during the working time of the composition.

Compositions which have a putty consistency to be used a void filler can be enhanced by incorporating macro porous granules or chips to allow for new bone ingrowth. These granules may come from synthetic sources such α-TCP or β-TCP granules or it may be preferred to select the granules or chips from autologous bone sources or demineralized bone to enhance the bone healing rate.

It is further envisioned that the cement compositions disclosed herein may be packaged into kits that may include a vial containing the TTCP with the small amino acid phosphate species pre-filled together and packaged under vacuum, nitrogen, or dry air to preserve the shelf life. Further, if additives are used, they may be included within this vial or in a separate vial. The aqueous medium is provided in a separate vial. The kit may include mixing bowls, stirring sticks, spatulas, syringes, and/or any other desirable component for application.

Composition of the current disclosure are envisioned to provide ease of use in different medical applications based on ease of application, duration of use before cure, resistance to in vivo environments, extended maneuverability of bone fragments and/or implant devices prior to cure onset, good load bearing capabilities after cure, and good ultimate bond strength. For example, compositions may have an adequate working period after mixing sometimes up to about 15 minutes depending on the application requirement, typically up to about 8 minutes or less, and preferably up to about 5 minutes or less. Further, the relative force of pressure required to inject the composition from an appropriately sized syringe may remain constant or below a certain injection force threshold from the point of mixing and loading the syringe to the end of the working period. It is contemplated that bone fragments adhered together or implanted devices may exhibit moderate separation strengths within the working period. Such moderate separation strengths may be exhibited regardless of the relative compressive force used during apposition. It is further contemplated that cement compositions of the present disclosure may have sufficient material cohesion when applied in moist, wet, greasy and/or fatty saline environments, such as in vivo settings, thereby reducing the need for surface preparation and maintaining a dry environment. As well, good capacity for supporting passive movement and maintaining load and non-load bearing bone fragment alignment after surgery during initial rehabilitation period and active range of motion rehabilitation period are envisioned for cement compositions contemplated herein.

Typical compositions exhibit an adhesive strength upon curing, typically after greater than about 10 minutes from initial mixing, in the range of about 250 to about 2000 kPa on cancellous bone and from about 250 to about 10,000 kPa on cortical bone in at least one of compression, tension, shear, and/or bending. Compositions can be chosen to achieve the strength in these ranges; the level of strength required is dependent upon the clinical application. Also, it is important to note that the curing can be accomplished either in a wet environment, such as in bodily fluids, or in a dry environment, and the ultimate strength of the bond after cure does not seem to be significantly affected.

In the following examples all shear, tension and bending testing was done using an Instron Force test machine (Model #5564) setup as follows. For shear testing, the sample was supported and fastened to the machine at one end of the sample and the other end was left free and unsupported. For shear testing the samples have a bond surface that was 90° to the face of the bone samples unless there was an indication that the bond surface was at an angle of 45° from the face of the bone surface. The force test probe was placed in plane against the top of the bond line of the sample and force was applied until failure. For tension testing each end of the sample was clamped to the testing machine and the force was applied at 90° to the bond to pull the sample apart. When the bond fails the result was recorded. For the 3 point bending testing each end of the sample was supported without clamping the sample to create a span distance of 35 mm. Force was applied by the force probe to the top of the sample at the center point (same position as the bond line) between both ends until the bond fails. The TTCP that was used in all the following examples was a commercially available material that included from about 17% to 32% of related impurities. These materials all contained about 68% to 83% TTCP.

Example 1

A cement formulation having the following formulation: 250 mg OPLS, 400 mg TTCP, and 133 μl of water was mixed and applied to a 10 mm×10 mm×2 mm thick sheet of either 10/90 PLGA or 50/50 PLGA as shown in the table and to a cortical bone cube. Before strength testing the samples were allowed to cure for 10 minutes submersed in water at 30° C. The test was repeated 6 times and compared to two commercially available calcium phosphate based bone cements that were mixed in accord with label directions.

Example 1

PLGA Square Adhesion to Bovine Cortical Bone, 10 Min Cure

|  | Example | | | | | |
|---|---|---|---|---|---|---|
|  | 1A<br>TOM 250 (MPa) | 1B | Comp. 1A<br>HydroSet (MPa) | Comp. 1B | Comp. 1C<br>Norian (MPa) | Comp. 1D |
|  | PLGA<br>10/90 | PLGA<br>50/50 | PLGA<br>10/90 | PLGA<br>50/50 | PLGA<br>10/90 | PLGA<br>50/50 |
|  | 0.64 | 0.35 | 0.16 | 0.12 | 0.07 | 0.05 |
|  | 0.72 | 0.38 | 0.08 | 0.08 | 0.2 | 0.01 |
|  | 0.96 | 0.43 | 0.11 | 0.12 | 0.03 | 0.03 |
|  | 0.83 | 0.47 | 0.23 | 0.08 | 0.12 | 0.05 |
|  | 0.99 | 0.34 | 0.22 | 0.04 | 0.14 | 0.01 |
|  | 0.69 | 0.42 | 0.13 | 0.03 | 0.09 |  |
| average | 0.81 | 0.40 | 0.16 | 0.08 | 0.11 | 0.03 |
| St. Dev. | 0.15 | 0.05 | 0.06 | 0.04 | 0.06 | 0.02 |

Figure 2:
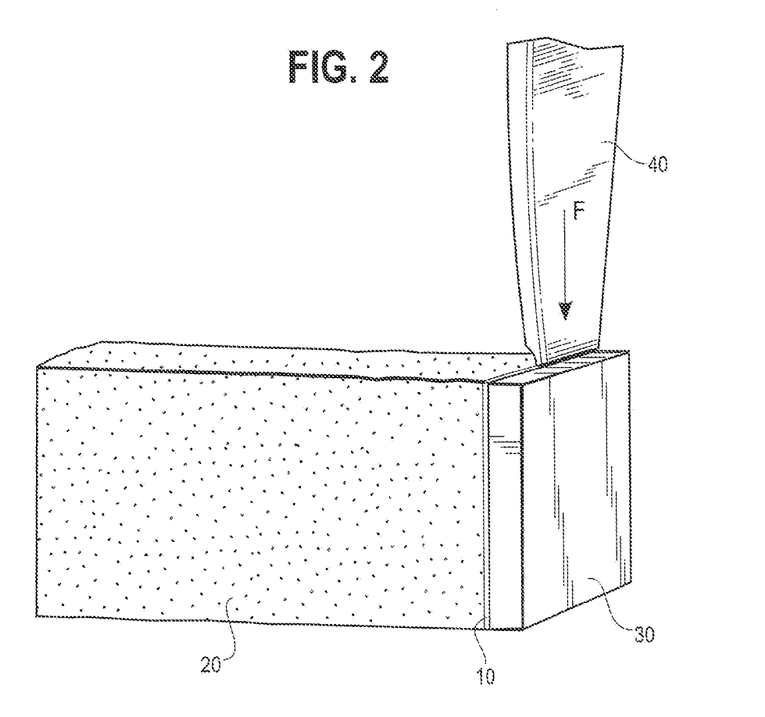
FIG. 2 is a representation of the test setup for testing the strength of the bond between bone and a polymer sheet.
Figure 3:
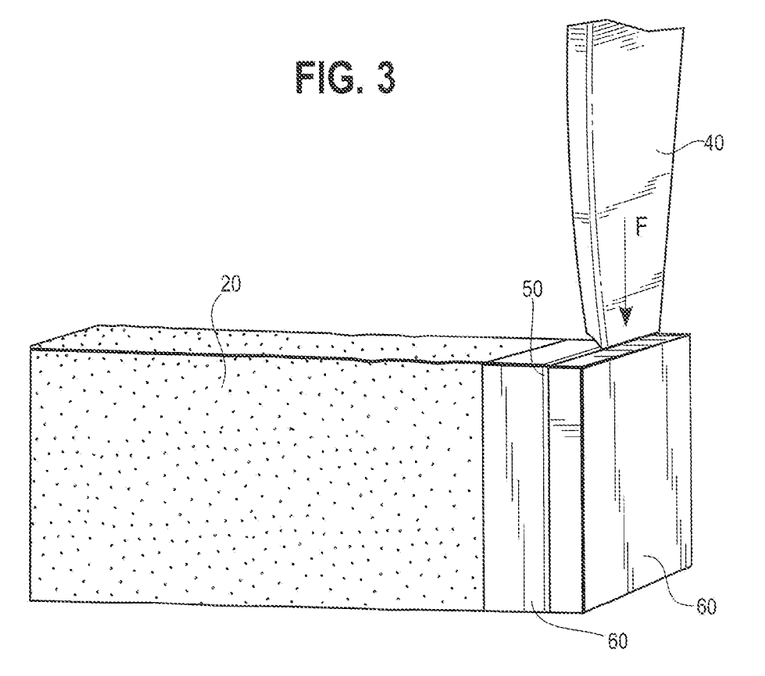
FIG. 3 is a representation of the test setup for testing the strength of the bond between two polymer sheets.

As shown in FIG. 2, a small amount (10) of the above formulations was applied both to cortical bone (20) that has been clamped in place (clamps not shown for clarity) and to the appropriate PLGA sheet (30) and tested using a shear testing device (40) (blade only shown for clarity) with a force vector (F) applied directly to the cement bond (10). As seen from the data, the formulations of Examples 1A and 1B had significantly higher shear strength than the Comparative Examples 1A-D.

Example 2

A cement formulation having the following formulation: 250 mg OPLS, 400 mg TTCP, and 133 μl of water was mixed and applied between two 10 mm×10 mm×2 mm thick sheets of either 10/90 PLGA or 50/50 PLGA as shown in the table. Before strength testing the samples were allowed to cure for 10 minutes submersed in water at 30° C. The test was repeated at minimum 6 times and compared to two commercially available calcium phosphate based bone cements that were mixed in accord with label directions.

Example 2

PLGA Square Adhesion to PLGA Square, 10 Min Cure

|  | Example | | | | | |
|---|---|---|---|---|---|---|
|  | 2A<br>TOM 250 (MPa) | 2B | Comp. 2A<br>HydroSet (MPa) | Comp. 2B | Comp. 2C<br>Norian (MPa) | Comp. 2D |
|  | PLGA<br>10/90 | PLGA<br>50/50 | PLGA<br>10/90 | PLGA<br>50/50 | PLGA<br>10/90 | PLGA<br>50/50 |
|  | 0.64 | 0.35 | 0.16 | 0.12 | 0.07 | 0.05 |
|  | 0.72 | 0.38 | 0.08 | 0.08 | 0.2 | 0.01 |
|  | 0.96 | 0.43 | 0.11 | 0.12 | 0.03 | 0.03 |
|  | 0.83 | 0.47 | 0.23 | 0.08 | 0.12 |  |
|  | 0.99 | 0.34 | 0.22 | 0.04 | 0.14 |  |
|  | 0.69 | 0.42 | 0.13 | 0.03 | 0.09 |  |
| average | 0.81 | 0.40 | 0.16 | 0.08 | 0.11 | 0.03 |
| St. Dev. | 0.15 | 0.05 | 0.06 | 0.04 | 0.06 | 0.02 |

As shown in FIG. 2, a small amount (50) of each of the above formulations was applied both to the appropriate PLGA sheets (60) and the sheets were pressed together and tested using the same shear testing device with a force (F) applied directly to the cement bond. The one polymer sheet (6) was adhered to cortical bone (20) that has been clamped in place (clamps not shown for clarity). As seen from the data, the formulations of Examples 2A and 2B had significantly higher shear strength than the Comparative Examples 2A-2D.

Example 3

In order to see the effect on the intrinsic material strength, polymer fibers were added to the compositions to form an interpenetrating network. A series of compositions set out in Table 1 were prepared and tested as follows. Each composition was mixed for 20 seconds in a polycarbonate bowl using either a polycarbonate pestle or spatula. After mixing, the composition was applied to both surfaces of bovine cortical bone cubes that had apposing faces using a spatula. The faces were created with a 90° angle for the bending tests (9×9.5 mm face). Prior to testing, the bone cubes were incubated within a phosphate buffered saline (PBS), solution bath at 30° C. and had pre-dampened surfaces during composition application. By 90 seconds from the start of mixing, the apposing faces were adhered together and aligned with minimal hand compression force for 10 seconds and were immediately transferred and submerged within a PBS solution bath held at 30° C. for the duration of 10 minutes. After the samples cured, the cubes were loaded onto the 3pt bending sample fixture and tested on an Instron force test machine. The compositions that form an interpenetrating network with polymer fibers (3A & 3B) show increased bending strength compared to the fiber free composition (Comparative Example 3) that does not form an interpenetrating polymer network system.

TABLE 1

| Composition | Comp. Ex. 3 | 3A | 3B |
|---|---|---|---|
| TTCP | 400 mg | 400 mg | 400 mg |
| Phosphoserine | 185 mg | 250 mg | 250 mg |
| Water | 130 μl | 175 μl | 175 μl |
| β-TCP granules | 100 mg | 133 mg | 133 mg |
| Calcium carbonate powder | 14 mg | 14 mg | 14 mg |
| Silk, braided & ground fiber |  | 7 mg |  |
| PLGA (10:90) fiber |  |  | 25 mg |
| 3 pt Bending Strength (MPa) | 0.75 MPa | 5.65 MPa | 4.68 MPa |

Example 4

The procedure of Example 2 was repeated except that the PLGA sheets were replace by polycarbonate and acrylic sheets. The surface treatment on these sheets was removed by rubbing the surface with the edge of a glass slide. The polycarbonate sheet was clear polycarbonate sheet 0.236 inches thick (part 8574K11) and the acrylic sheet was clear 0.25 inch thick acrylic sheet (part 8560K354), both available from McMaster-Carr, Aurora, Ohio. An attempt was made to test the Norian cement as was done in Example 2 however the Norian cements displayed no adhesion to the polycarbonate or acrylic sheets and the cement disintegrated over time in a wet environment. The test was repeated at minimum 6 times.

Example 4

Other Polymer Square Adhesion to Other Polymer, 10 Min Cure

| | Example | |
|---|---|---|
| | 4A | 4B |
| | TOM 250 | |
| | Polycarbonate | Acrylic |
| | 0.79 MPa | 1.36 MPa |
| | 0.8 MPa | 1.39 MPa |
| | 0.51 MPa | 1.25 MPa |
| | 0.73 MPa | 0.74 MPa |
| | 0.72 MPa | 0.67 MPa |
| | 0.71 MPa | 0.58 MPa |
| average | 0.71 MPa | 1.00 MPa |
| St. Dev. | 0.10 MPa | 0.37 MPa |

INDUSTRIAL APPLICATION

Cement compositions disclosed herein provide adhesive and cohesive strength through mechanical and chemical interlocking with bone substrates. The cement formulations have a tack and/or sticky quality that allows temporary adherence early in the curing process and a delay in significant curing early on. The cement formulations may mimic natural bone architecture and provide superior mechanical strength over longer periods of time relative to convention cement formulations.

The disclosure has been presented in an illustrative manner in order to enable a person of ordinary skill in the art to make and use the disclosure, and the terminology used is intended to be in the nature of description rather than of limitation. It is understood that the disclosure may be practiced in ways other than as specifically disclosed, and that all modifications, equivalents, and variations of the present disclosure, which are possible in light of the above teachings and ascertainable to a person of ordinary skill in the art, are specifically included within the scope of the impending claims. All patents, patent publications, and other references cited herein are incorporated herein by reference.

What we claim is:

1. A non-covalently bonded interpenetrating network comprising a reactive mixture of an amino acid phosphate species, tetracalcium phosphate, and a polymeric material that contains functional groups comprising electronegative atoms as the bonding sites of the polymer surfaces to the available metal ions, in an aqueous environment, wherein the polymeric material comprises a powder and the concentration of the amino acid phosphate species is greater than about 100 mM.

2. The network of claim 1 wherein;
   (i) the polymeric material comprises an ester, carbonyl, carbonate, carboxylic acid, amide, amine, or a mixture thereof,
   (ii) the amino acid phosphate species is a compound of the formula;

where A is O, $CH_2$, or S; R is H, $NH_2$, $NHCO(CH_2)_tCH_3$ where t is 0 to 2, $NH(CH_2)_xCH_3$ where x is 0 to 3, $NR_1R_2$ where $R_1$ is $(CH_2)_yCH_3$ and $R_2$ is $(CH_2)_yCH_3$ where y is 0 to 2, $(CH_2)_zCH_3$ where z is 0 to 3; m is 0 to 1; n is 0 to 3, and (iii) the aqueous environment is an aqueous medium.

3. The network as described in claim 2, wherein the polymeric material is selected from the group consisting of poly (L-lactide), poly(D,L-lactide), polyglycolide, poly(ε-caprolactone), polycarbonate, poly(teramethylglycolic-acid), poly (dioxanone), poly(hydroxybutyrate), poly(hydroxyvalerate), poly(L-lactide-co-glycolide), poly(glycolide-co-trimethylene-carbonate), poly(glycolide-co-caprolactone), poly(glycolide-co-dioxanone-co-trimethylene-carbonate), poly(tetramethylglycolic-acid-co-dioxanone-co-trimethylene-carbonate), poly(glycolide-co-caprolactone-co-L-lactide-co-trimethylene-carbonate), poly(hydroxybutyrate-co-hydroxyvalerate), poly(methyl-methacrylate), poly (acrylate), polyamines, polyimidazoles, poly(vinyl-pyrrolidone), silk, chitosan, hyaluronic acid, gelatin, and a copolymer or mixture thereof.

4. The network as described in claim 1, wherein the polymeric material is a linear homopolymer, a linear copolymer, a cross linked polymer, a block polymer, a branched polymer, a hyper branched polymer, a star shaped polymer or a mixture thereof.

5. The network as described in claim 2, wherein the amino acid phosphate species is phosphoserine.

6. The network as described in claim 1 wherein:
   (i) the tetracalcium phosphate is present in an amount from about 10 to about 89.9 weight percent based on the weight of the combination of the tetracalcium phosphate, the polymeric material, and the amino acid phosphate species; and
   (ii) the polymeric material is present in an amount from about 0.1 to about 75 weight percent based on the weight of the combination of the tetracalcium phosphate, the polymeric material, and the amino acid phosphate species.

7. A bone restorative composition comprising:
   (i) tetracalcium phosphate,
   (ii) a polymeric material comprising an ester, carbonyl, carbonate, carboxylic acid, amide, amine or a mixture thereof as the bonding site of the polymer surfaces to the available metal ions, wherein the polymeric material comprises a powder, (iii) a compound of the formula;

where A is O, CH$_2$, or S; R is H, NH$_2$, NHCO(CH$_2$)$_t$CH$_3$ where t is 0 to 2, NH(CH$_2$)$_x$CH$_3$ where x is 0 to 3, NR$_1$R$_2$ where R$_1$ is (CH$_2$)$_y$CH$_3$ and R$_2$ is (CH$_2$)$_y$CH$_3$ where y is 0 to 2, (CH$_2$)$_z$CH$_3$ where z is 0 to 3; m is 0 to 1, n is 0 to 3; and wherein the compound is present at a concentration greater than about 100 mM; and (iv) an aqueous medium.

8. The bone restorative composition as described in claim 7 wherein the polymeric material is selected from the group consisting of poly(L-lactide), poly(D,L-lactide), polyglycolide, poly(ε-caprolactone), poly(teramethylglycolic-acid), poly(dioxanone), poly(hydroxybutyrate), poly(hydroxyvalerate), poly(L-lactide-co-glycolide), poly(glycolide-co-trimethylene-carbonate), poly(glycolide-co-caprolactone), poly(glycolide-co-dioxanone-co-trimethylene-carbonate), poly(tetramethylglycolic-acid-co-dioxanone-co-trimethylene-carbonate), poly(glycolide-co-caprolactone-co-L-lactide-co-trimethylene-carbonate), poly(hydroxybutyrate-co-hydroxyvalerate), poly(methyl-methacrylate), poly(acrylate), polyamines, polyimidazoles, poly(vinyl-pyrrolidone), silk, chitosan, hyaluronic acid, gelatin, and a copolymer or mixture thereof.

9. The bone restorative composition as described in claim 7 wherein the polymeric material is a linear homopolymer, a linear copolymer, a cross linked polymer, a block polymer, a branched polymer, a hyper branched polymer, a star shaped polymer, or a mixture thereof.

10. The bone restorative composition as described in claim 7 wherein the compound of component (iii) is phosphoserine.

11. The bone restorative composition as described in claim 7 wherein:

(i) the tetracalcium phosphate is present in an amount from about 10 to about 89.9 weight percent based on the weight of the combination of the tetracalcium phosphate, the polymeric material, and the compound; and (ii) the polymeric material is present in an amount from about 0.1 to about 75 weight percent based on the weight of the combination of the tetracalcium phosphate, the polymeric material, and the compound.

12. A kit for restoring bone comprising;

A) a first container containing a composition comprising:
(i) tetracalcium phosphate,
(ii) a polymer comprising an ester, carbonyl, carbonate, carboxylic acid, amide, amine, or a mixture thereof as the bonding site of the polymer surfaces to the available metal ions, wherein the polymeric material comprises a powder, and
(iii) a compound of the formula;

where A is O, CH$_2$, or S; R is H, NH$_2$, NHCO(CH$_2$)$_t$CH$_3$ where t is 0 to 2, NH(CH$_2$)$_x$CH$_3$ where x is 0 to 3, NR$_1$R$_2$ where R$_1$ is (CH$_2$)$_y$CH$_3$ and R$_2$ is (CH$_2$)$_y$CH$_3$ where y is 0 to 2, (CH$_2$)$_z$CH$_3$ where z is 0 to 3; m is 0 to 1; n is 0 to 3; and B) a second container containing an aqueous medium;
wherein upon mixing the contents of the first container with the contents of the second container, the resulting composition comprises a compound of component (iii) at a concentration greater than about 100 mM.

13. The kit as described in claim 12 wherein the polymeric material is selected from the group consisting of poly(L-lactide), poly(D,L-lactide), polyglycolide, poly(ε-caprolactone), poly(teramethylglycolic-acid), poly(dioxanone), poly(hydroxybutyrate), poly(hydroxyvalerate), poly(L-lactide-co-glycolide), poly(glycolide-co-trimethylene-carbonate), poly(glycolide-co-caprolactone), poly(glycolide-co-dioxanone-co-trimethylene-carbonate), poly(tetramethylglycolic-acid-co-dioxanone-co-trimethylene-carbonate), poly(glycolide-co-caprolactone-co-L-lactide-co-trimethylene-carbonate), poly(hydroxybutyrate-co-hydroxyvalerate), poly(methyl-methacrylate), poly(acrylate), polyamines, polyimidazoles, poly(vinyl-pyrrolidone), silk, chitosan, hyaluronic acid, gelatin, and a copolymer or mixture thereof.

14. The kit as described in claim 12 wherein the polymeric material is a linear homopolymer, a linear copolymer, a cross linked polymer, a block polymer, a branched polymer, a hyper branched polymer, a star shaped polymer, or a mixture thereof.

15. The kit as described in claim 12 wherein the compound of component (iii) is phosphoserine.

16. The kit as described in claim 12 wherein:
(i) the tetracalcium phosphate is present in an amount from about 10 to about 89.9 weight percent based on the weight of the combination of the tetracalcium phosphate, the polymeric material, and the compound; and
(ii) the polymeric material is present in an amount from about 0.1 to about 75 weight percent based on the weight of the combination of tetracalcium phosphate, the polymeric material, and the compound.

17. The network of claim 1, wherein the concentration of the amino acid phosphate species is greater than about 1 M.

18. The network of claim 3, wherein the polymeric material is selected from the group consisting of poly(L-lactide), poly(D,L-lactide), polyglycolide, poly(teramethylglycolic-acid), poly(hydroxyvalerate), poly(L-lactide-co-glycolide), poly(glycolide-co-caprolactone), and poly(acrylate).

19. The composition of claim 7, wherein the concentration of the compound of component (iii) is greater than about 1M.

20. The composition of claim 8, wherein the polymeric material is selected from the group consisting of poly(L-lactide), poly(D,L-lactide), polyglycolide, poly(teramethylglycolic-acid), poly(hydroxyvalerate), poly(L-lactide-co-glycolide), poly(glycolide-co-caprolactone), and poly(acrylate).

21. The kit of claim 12, wherein upon mixing the contents of the first container with the contents of the second container, the resulting composition comprises a compound of component (iii) at a concentration greater than about 1 M.

22. The kit of claim 13, wherein the polymeric material is selected from the group consisting of poly(L-lactide), poly(D,L-lactide), polyglycolide, poly(teramethylglycolic-acid), poly(hydroxyvalerate), poly(L-lactide-co-glycolide), poly(glycolide-co-caprolactone), and poly(acrylate).

23. An adhesive composition comprising a reactive mixture of an amino acid phosphate species, tetracalcium phosphate, and a synthetic polymeric material that contains functional groups comprising electronegative atoms as the bonding sites of the polymer surfaces to the available metal ions, in an aqueous environment, wherein the synthetic polymeric material comprises a powder.

24. The adhesive composition of claim 23, wherein;
(i) the synthetic polymeric material comprises an ester, carbonyl, carbonate, carboxylic acid, amide, amine, or a mixture thereof,
(ii) the amino acid phosphate species is a compound of the formula;

where A is O, $CH_2$, or S; R is H, $NH_2$, $NHCO(CH_2)_tCH_3$ where t is 0 to 2, $NH(CH_2)_xCH_3$ where x is 0 to 3, $NR_1R_2$ where $R_1$ is $(CH_2)_yCH_3$ and $R_2$ is $(CH_2)_yCH_3$ where y is 0 to 2, $(CH_2)_zCH_3$ where z is 0 to 3; m is 0 to 1; n is 0 to 3, and wherein the compound is present in an amount greater than about 10% by weight based on the combined weight of the tetracalcium phosphate and the compound, and
(iii) the aqueous environment is an aqueous medium.

25. The adhesive composition of claim 23, wherein the synthetic polymeric material is selected from the group consisting of poly(L-lactide), poly(D,L-lactide), polyglycolide, poly(ε-caprolactone), polycarbonate, poly(teramethylglycolic-acid), poly(dioxanone), poly(hydroxybutyrate), poly(hydroxyvalerate), poly(L-lactide-co-glycolide), poly(glycolide-co-trimethylene-carbonate), poly(glycolide-co-caprolactone), poly(glycolide-co-dioxanone-co-trimethylene-carbonate), poly(tetramethylglycolic-acid-co-dioxanone-co-trimethylene-carbonate), poly(glycolide-co-caprolactone-co-L-lactide-co-trimethylene-carbonate), poly(hydroxybutyrate-co-hydroxyvalerate), poly(methylmethacrylate), poly(acrylate), polyamines, polyimidazoles, poly(vinyl-pyrrolidone), and a copolymer or mixture thereof.

26. The adhesive composition of claim 25, wherein the synthetic polymeric material is selected from the group consisting of poly(L-lactide), poly(D,L-lactide), polyglycolide, poly(teramethylglycolic-acid), poly(hydroxyvalerate), poly(L-lactide-co-glycolide), poly(glycolide-co-caprolactone), and poly(acrylate).

27. The adhesive composition as described in claim 23, wherein the polymeric material is a linear homopolymer, a linear copolymer, a cross linked polymer, a block polymer, a branched polymer, a hyper branched polymer, a star shaped polymer or a mixture thereof.

28. The adhesive composition of claim 24, wherein the amino acid phosphate species is phosphoserine.

29. The adhesive composition of claim 23, wherein:
(i) the tetracalcium phosphate is present in an amount from about 10 to about 89.9 weight percent based on the weight of the combination of the tetracalcium phosphate, the polymeric material, and the amino acid phosphate species;
(ii) the polymeric material is present in an amount from about 0.1 to about 75 weight percent based on the weight of the combination of the tetracalcium phosphate, the polymeric material, and the amino acid phosphate species; and
(iii) the amino acid phosphate species is present in an amount from about 10 to about 89.9 weight percent based on the weight of the combination of the tetracalcium phosphate, the polymeric material, and the amino acid phosphate species.

30. An adhesive composition comprising a reactive mixture of an amino acid phosphate species, tetracalcium phosphate, and a polymeric material that contains functional groups comprising electronegative atoms as the bonding sites of the polymer surfaces to the available metal ions, in an aqueous environment wherein the polymeric material comprises a powder and the adhesive strength of the composition upon curing is greater than 10 kPa.

31. The adhesive composition of claim 30 wherein;
(i) the polymeric material comprises an ester, carbonyl, carbonate, carboxylic acid, amide, amine, or a mixture thereof,
(ii) the amino acid phosphate species is a compound of the formula;

where A is O, $CH_2$, or S; R is H, $NH_2$, $NHCO(CH_2)_tCH_3$ where t is 0 to 2, $NH(CH_2)_xCH_3$ where x is 0 to 3, $NR_1R_2$ where $R_1$ is $(CH_2)_yCH_3$ and $R_2$ is $(CH_2)_yCH_3$ where y is 0 to 2, $(CH_2)_zCH_3$ where z is 0 to 3; m is 0 to 1; n is 0 to 3, and wherein the compound is present in an amount greater than about 10% by weight based on the combined weight of the tetracalcium phosphate and the compound, and
(iii) the aqueous environment is an aqueous medium.

32. The adhesive composition as described in claim 30, wherein the polymeric material is selected from the group consisting of poly(L-lactide), poly(D,L-lactide), polyglycolide, poly(ε-caprolactone), polycarbonate, poly(teramethylglycolic-acid), poly(dioxanone), poly(hydroxybutyrate), poly(hydroxyvalerate), poly(L-lactide-co-glycolide), poly(glycolide-co-trimethylene-carbonate), poly(glycolide-co-caprolactone), poly(glycolide-co-dioxanone-co-trimethylene-carbonate), poly(tetramethylglycolic-acid-co-dioxanone-co-trimethylene-carbonate), poly(glycolide-co-caprolactone-co-L-lactide-co-trimethylene-carbonate), poly(hydroxybutyrate-co-hydroxyvalerate), poly(methylmethacrylate), poly(acrylate), polyamines, polyimidazoles, poly(vinyl-pyrrolidone), silk, chitosan, hyaluronic acid, gelatin, and a copolymer or mixture thereof.

33. The adhesive composition as described in claim 30, wherein the polymeric material is a linear homopolymer, a linear copolymer, a cross linked polymer, a block polymer, a branched polymer, a hyper branched polymer, a star shaped polymer, or a mixture thereof.

34. The adhesive composition as described in claim 30, wherein the amino acid phosphate species is phosphoserine.

35. The adhesive composition as described in claim 30, wherein:
(i) the tetracalcium phosphate is present in an amount from about 10 to about 89.9 weight percent based on the weight of the combination of the tetracalcium phosphate, the polymeric material, and the amino acid phosphate species;
(ii) the polymeric material is present in an amount from about 0.1 to about 75 weight percent based on the weight of the combination of the tetracalcium phosphate, the polymeric material, and the amino acid phosphate species; and (iii) the amino acid phosphate species is present in an amount from about 10 to about 89.9 weight percent based on the weight of the combination of the tetracalcium phosphate, the polymeric material, and the amino acid phosphate species.

\* \* \* \* \*